United States Patent
Tarunaga (10) Patent No.: US 11,617,869 B2
(45) Date of Patent: Apr. 4, 2023

(54) BALLOON CATHETER AND METHOD FOR MANUFACTURING MEDICAL ELONGATED BODY

(71) Applicant: TERUMO KABUSHIKI KAISHA, Tokyo (JP)

(72) Inventor: Akihiko Tarunaga, Ebina (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 815 days.

(21) Appl. No.: 16/585,037

(22) Filed: Sep. 27, 2019

(65) Prior Publication Data
US 2020/0023171 A1 Jan. 23, 2020

Related U.S. Application Data (63) Continuation of application No. PCT/JP2018/012437, filed on Mar. 27, 2018.

(30) Foreign Application Priority Data

Mar. 31, 2017 (JP) .............................. JP2017-072815

(51) Int. Cl.
*A61M 25/10* (2013.01)
*A61M 25/09* (2006.01)

(52) U.S. Cl.
CPC .... *A61M 25/1025* (2013.01); *A61M 25/1034* (2013.01); *A61M 25/1036* (2013.01);
(Continued)

(58) Field of Classification Search
CPC .......... A61M 25/1025; A61M 25/1034; A61M 25/1036; A61M 2025/09008;
(Continued)

(56) References Cited

U.S. PATENT DOCUMENTS

| 5,154,725 A | * | 10/1992 | Leopold | .............. A61M 25/104 606/194 |
| 2004/0098081 A1 | | 5/2004 | Landreville et al. | |
| 2005/0059959 A1 | * | 3/2005 | Eidenschink | ....... A61M 25/104 604/534 |

(Continued)

FOREIGN PATENT DOCUMENTS

| CN | 101902988 A | 12/2010 |
| CN | 103191509 A | 7/2013 |

(Continued)

OTHER PUBLICATIONS

Office Action (The Third Office Action) dated Mar. 2, 2022, by the State Intellectual Property Office of People's Republic of China in corresponding Chinese Patent Application No. 201880021472.1 and an English Translation of the Office Action. (15 pages).

(Continued)

*Primary Examiner* — Amber R Stiles
(74) *Attorney, Agent, or Firm* — Buchanan Ingersoll & Rooney PC (57) ABSTRACT

A balloon catheter and method for manufacturing are disclosed in which the fracturing of the vicinity of a proximal opening portion formed by an inner shaft can be prevented. A distal side of an inner shaft included by a balloon catheter is disposed in a lumen of an outer distal shaft, and a proximal side of the inner shaft is disposed on an outer surface of an outer proximal shaft, and the inner shaft forms a proximal opening portion which opens on an outer surface side of the outer proximal shaft. The inner shaft has a first region and a second region disposed on a proximal side of the first region. The first region is fixed to the outer surface of the outer proximal shaft. The second region is not fixed to the outer surface of the outer proximal shaft.

17 Claims, 6 Drawing Sheets

(52) U.S. Cl.
CPC ............. *A61M 2025/09008* (2013.01); *A61M 2025/09116* (2013.01)

(58) Field of Classification Search
CPC .... A61M 2025/09116; A61M 25/0043; A61M 25/0052; A61M 25/1006; A61M 2025/0183; A61M 25/01
See application file for complete search history.

(56) References Cited

U.S. PATENT DOCUMENTS

| | | |
|---|---|---|
| 2007/0142821 A1 | 6/2007 | Hennessy et al. |
| 2008/0045928 A1 | 2/2008 | Simpson et al. |
| 2010/0036360 A1 | 2/2010 | Herbowy et al. |
| 2015/0343183 A1 | 12/2015 | Kawase |
| 2017/0080181 A1 | 3/2017 | Shiono et al. |

FOREIGN PATENT DOCUMENTS

| | | |
|---|---|---|
| CN | 104981266 A | 10/2015 |
| JP | 2005211308 A | 8/2005 |
| JP | 2007501655 A | 2/2007 |
| JP | 2007505683 A | 3/2007 |
| JP | 2009542363 A | 12/2009 |
| JP | 2015093173 A | 5/2015 |

OTHER PUBLICATIONS

International Search Report (PCT/ISA/210) dated Jun. 12, 2018, by the Japanese Patent Office as the International Searching Authority for International Application No. PCT/JP2018/012437.

Written Opinion (PCT/ISA/237) dated Jun. 12, 2018, by the Japanese Patent Office as the International Searching Authority for International Application No. PCT/JP2018/012437.

The extended European Search Report dated Dec. 21, 2020, by the European Patent Office in corresponding European Patent Application No. 18777292.6-1132. (8 pages).

Office Action (The First Office Action) dated Feb. 19, 2021, by the National Intellectual Property Administration in corresponding Chinese Patent Application No. 201880021472.1 and an English Translation of the Office Action. (18 pages).

\* cited by examiner

BALLOON CATHETER AND METHOD FOR MANUFACTURING MEDICAL ELONGATED BODY

CROSS-REFERENCES TO RELATED APPLICATIONS

This application is a continuation of International Application No. PCT/JP2018/012437 filed on Mar. 27, 2018, which claims priority to Japanese Application No. 2017-072815 filed on Mar. 31, 2017, the entire content of both of which is incorporated herein by reference.

FIELD OF THE DISCLOSURE

The present disclosure generally relates to a balloon catheter and a method for manufacturing a medical elongated body.

BACKGROUND DISCUSSION

A balloon catheter is as a medical device that dilates a lesion area such as a stenosed site formed in a body lumen such as a blood vessel. Generally, there are an over-the-wire type balloon catheter and a rapid exchange type balloon catheter.

As described in JP-A-2015-93173, in the rapid exchange type balloon catheter, a guide wire is inserted into a guide wire lumen which is formed only on a distal side of a catheter shaft in which a balloon is disposed. For this reason, a guide wire port (proximal opening portion) through which the guide wire can be inserted into and removed from the guide wire lumen is provided at a predetermined position on the distal side of the catheter shaft in an axial direction (longitudinal direction).

In a catheter shaft used in the rapid exchange type balloon catheter, an outer distal shaft, an outer proximal shaft, and an inner shaft of the catheter shaft are integrated with each other by heat-welding (or heat-shrinking), and a guide wire port is formed in the vicinity of a proximal portion of the inner shaft. Note that each of the outer distal shaft and the outer proximal shaft is a tubular member forming an inflation lumen through which a pressurizing medium (for example, a working fluid) for inflating a balloon flows. The inner shaft can be a tubular member including a lumen forming a guide wire lumen.

In a procedure using the balloon catheter, an operator such as a physician inserts the guide wire into a lesion area such as a stenosed site formed in a blood vessel. The operator inserts a proximal side of the guide wire into the guide wire lumen from a distal side of the inner shaft, and causes the guide wire to come out from the guide wire lumen through the guide wire port on the proximal side of the inner shaft. The operator guides the balloon of the balloon catheter to the lesion area by moving the balloon catheter along the guide wire.

In the middle of the procedure, the operator moves the guide wire to a proximal side or a distal side in a state where the guide wire is inserted into the guide wire lumen of the balloon catheter, and takes the guide wire out from a proximal opening portion of the inner shaft. When the operator performs such operation, if stress is excessively concentrated in the vicinity of the guide wire port of the inner shaft, the inner shaft of the balloon catheter may be fractured. If the guide wire is caught in a fractured portion (torn-out portion) of the inner shaft, since the operator has difficulties in smoothly moving the guide wire, the operability of the guide wire can deteriorate remarkably.

SUMMARY

A balloon catheter is disclosed in which the vicinity of the proximal opening portion formed by the inner shaft can be prevented from being fractured and to provide a method for manufacturing a medical elongated body.

According to the present disclosure, a balloon catheter is disclosed, which includes an inner shaft; an outer shaft covering a part of the inner shaft; and a balloon fixed to the inner shaft and the outer shaft. The outer shaft has an outer distal shaft having a lumen, and an outer proximal shaft fixed to a proximal side of the outer distal shaft and having a lumen communicating with the lumen of the outer distal shaft. A distal side of the inner shaft is disposed in the lumen of the outer distal shaft, a proximal side of the inner shaft is disposed on an outer surface of the outer proximal shaft, and the inner shaft forms a proximal opening portion which opens on an outer surface side of the outer proximal shaft. The inner shaft has a first region and a second region disposed on a proximal side of the first region, in a range from a proximal end of the outer distal shaft disposed on the outer surface of the outer proximal shaft to the proximal opening portion. The first region is fixed to the outer surface of the outer proximal shaft. The second region is not fixed to the outer surface of the outer proximal shaft.

In addition, according to the present disclosure, a method is disclosed for manufacturing a medical elongated body, the method including supplying an outer distal shaft, an outer proximal shaft, an inner shaft, a first mandrel to be disposed in a lumen of the inner shaft, and a second mandrel to be disposed in a lumen of the outer distal shaft and a lumen of the outer proximal shaft; disposing the inner shaft in the lumen of the outer distal shaft; inserting the first mandrel into the lumen of the inner shaft; disposing the outer proximal shaft such that a distal side of the inner shaft is disposed in the lumen of the outer distal shaft and a proximal side of the inner shaft is disposed on an outer surface of the outer proximal shaft; inserting the second mandrel into the lumen of the outer distal shaft and the lumen of the outer proximal shaft; disposing a heat shrinkable tube so as to cover a proximal end of the outer distal shaft, a distal end of the outer proximal shaft, and the inner shaft; positioning a proximal end of the heat shrinkable tube closer to a distal side than a proximal end of the inner shaft; and joining together the outer distal shaft, the outer proximal shaft, and the inner shaft in a state where the heat shrinkable tube is shrunk by applying heat to the heat shrinkable tube and the proximal end of the inner shaft is not joined by the heat shrinkable tube.

According to an aspect, the second region positioned on the proximal side of the inner shaft is not fixed to the outer surface of the outer proximal shaft. Therefore, for example, when the guide wire is being taken out from the proximal opening portion of the inner shaft, the foregoing configuration of the balloon catheter can help prevent stress from being concentrated in the vicinity of the proximal opening portion. In the balloon catheter, therefore, the inner shaft can be prevented from being fractured, and deterioration in the operability of the guide wire can be prevented, which would otherwise be induced by fracturing of the inner shaft. In addition, since the second region positioned on the proximal side of the inner shaft is not fixed to the outer surface of the outer proximal shaft, when the balloon catheter is delivered to a body lumen such as a curved blood vessel, the balloon catheter can be deformed rather easily such that the second region follows the guide wire. Therefore, the balloon catheter can improve the followability of the inner shaft with respect to the guide wire.

In the method for manufacturing a medical elongated body, when the inner shaft is being heat-welded to the outer shaft, since the proximal end of the inner shaft is not heat-welded by the heat shrinkable tube, the proximal end of the inner shaft is not fixed to the outer surface of the outer proximal shaft. Therefore, for example, when the guide wire is being taken out from the proximal opening portion of the inner shaft, stress can be prevented from being concentrated in the vicinity of the proximal end of the inner shaft in the medical elongated body manufactured by the manufacturing method. In addition, when being delivered to a body lumen such as a curved blood vessel, the vicinity of the proximal end of the inner shaft can be rather easily deformed to follow the guide wire, so that the inner shaft in the medical elongated body manufactured by the manufacturing method has an improved ability to follow the guide wire.

In accordance with an aspect, a balloon catheter is disclosed comprising: an inner shaft; an outer shaft covering a part of the inner shaft; a balloon fixed to the inner shaft and the outer shaft; the outer shaft having an outer distal shaft having a lumen, and an outer proximal shaft fixed to a proximal side of the outer distal shaft and having a lumen communicating with the lumen of the outer distal shaft; a distal side of the inner shaft is disposed in the lumen of the outer distal shaft, a proximal side of the inner shaft is disposed on an outer surface of the outer proximal shaft, and the inner shaft forms a proximal opening portion which opens on an outer surface side of the outer proximal shaft; the inner shaft having a first region and a second region disposed on a proximal side of the first region, in a range from a proximal end of the outer distal shaft disposed on the outer surface of the outer proximal shaft to the proximal opening portion; and wherein the first region is fixed to the outer surface of the outer proximal shaft, and the second region is not fixed to the outer surface of the outer proximal shaft.

In accordance with another aspect, a medical elongated body is disclosed, comprising: an inner shaft; an outer shaft covering a part of the inner shaft; the outer shaft having an outer distal shaft having a lumen, and an outer proximal shaft fixed to a proximal side of the outer distal shaft and having a lumen communicating with the lumen of the outer distal shaft; a distal side of the inner shaft is disposed in the lumen of the outer distal shaft, a proximal side of the inner shaft is disposed on an outer surface of the outer proximal shaft, and the inner shaft having a proximal opening portion on an outer surface side of the outer proximal shaft; the inner shaft on the proximal end having a first region and a second region, the second region being on a proximal side of the first region; and wherein the first region is joined to the outer surface of the outer proximal shaft, and the second region is not joined to the outer surface of the outer proximal shaft.

In accordance with an aspect, a method is disclosed for manufacturing a medical elongated body, the method comprising: supplying an outer distal shaft, an outer proximal shaft, an inner shaft, a first mandrel to be disposed in a lumen of the inner shaft, and a second mandrel to be disposed in a lumen of the outer distal shaft and a lumen of the outer proximal shaft; disposing the inner shaft in the lumen of the outer distal shaft; inserting the first mandrel into the lumen of the inner shaft; disposing the outer proximal shaft such that a distal side of the inner shaft is disposed in the lumen of the outer distal shaft and a proximal side of the inner shaft is disposed on an outer surface of the outer proximal shaft; inserting the second mandrel into the lumen of the outer distal shaft and the lumen of the outer proximal shaft; disposing a heat shrinkable tube to cover a proximal end of the outer distal shaft, a distal end of the outer proximal shaft, and the inner shaft; positioning a proximal end of the heat shrinkable tube closer to a distal side than a proximal end of the inner shaft; and joining the outer distal shaft, the outer proximal shaft, and the inner shaft to each other in a state where the heat shrinkable tube is shrunk by applying heat to the heat shrinkable tube, and wherein the proximal end of the inner shaft is not joined by the heat shrinkable tube to the outer surface of the outer proximal shaft.

BRIEF DESCRIPTION OF THE DRAWINGS

FIGS. 5A-5C show views for describing a method for manufacturing a medical elongated body according to the embodiment.

FIGS. 6A-6C show views for describing the method for manufacturing a medical elongated body according to the embodiment.

DETAILED DESCRIPTION

Set forth below with reference to the accompanying drawings is a detailed description of embodiments of a balloon catheter and a method for manufacturing a medical elongated body representing examples of the inventive a balloon catheter and a method for manufacturing a medical elongated body disclosed here. The dimensions or scales on the drawings may be exaggerated or different from actuality/reality for convenience of description and illustration.

Figure 1:
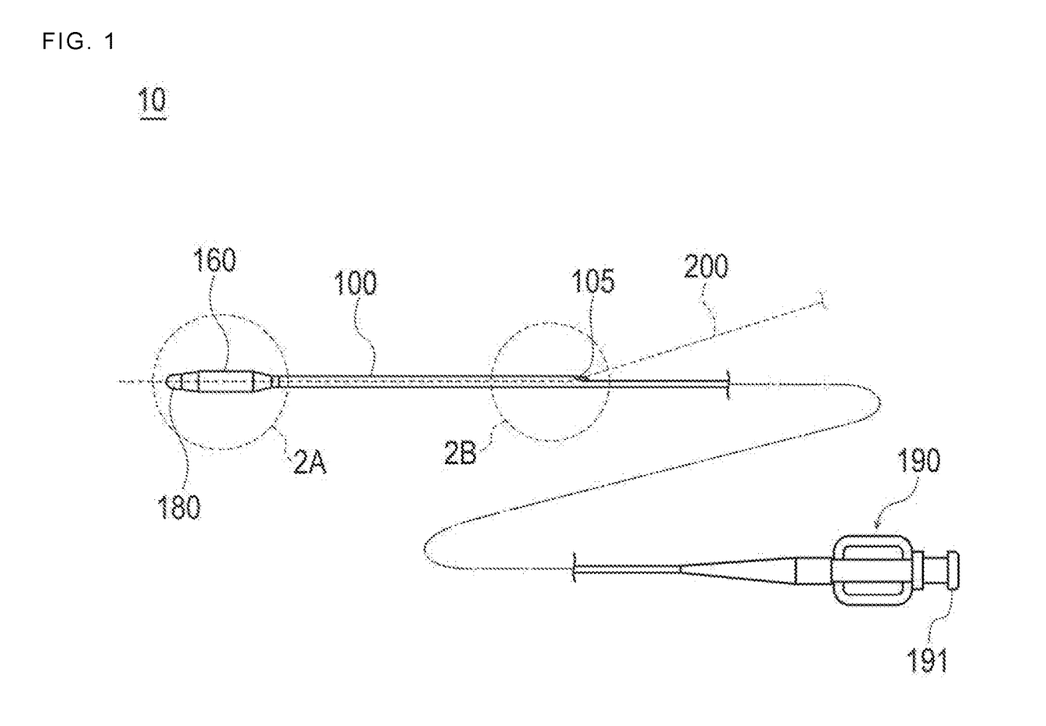
FIG. 1 is a view illustrating a balloon catheter according to an embodiment.

As illustrated in FIG. 1, a balloon catheter 10 according to an embodiment is a medical device that can widen and treat a lesion area such as a stenosed site formed in a body lumen by inflating a balloon 160, which is disposed on a distal side of a shaft 100, in the lesion area.

In accordance with an exemplary embodiment, the balloon catheter 10 can be a balloon catheter used in the PTCA treatment which is used to widen a stenosed site in a coronary artery. However, the balloon catheter 10 can also be a balloon catheter intended to treat a lesion area such as a stenosed site formed in body organs such as other blood vessels, biliary duct, trachea, esophagus, other digestive tracts, urethra, ear and nose cavity, and other organs.

Hereinbelow, the balloon catheter 10 will be described.

As illustrated in FIG. 1, in accordance with an exemplary embodiment, the balloon catheter 10 has an elongated shaft (equivalent to a "medical elongated body") 100; the balloon 160 disposed on the distal side of the shaft 100; and a hub 190 disposed on a proximal side of the shaft 100.

In the description of the embodiment, a side on which the balloon 160 is disposed refers to a distal side of the balloon catheter 10, a side on which the hub 190 is disposed refers to a proximal side of the balloon catheter 10, and an extending direction of the shaft 100 refers to an axial direction. In addition, in the description of the embodiment, a distal portion indicates a certain range containing a distal end (distal most end) and the vicinity of the distal end, and a proximal portion indicates a certain range containing a proximal end (proximal most end) and the vicinity of the proximal end.

As illustrated in FIG. 1, in accordance with an exemplary embodiment, the balloon catheter 10 can be a so-called rapid exchange type catheter in which a proximal opening portion (guide wire port) 105, through which a guide wire 200 can be inserted and removed, is formed close to the distal side of the shaft 100.

Figure 2A:
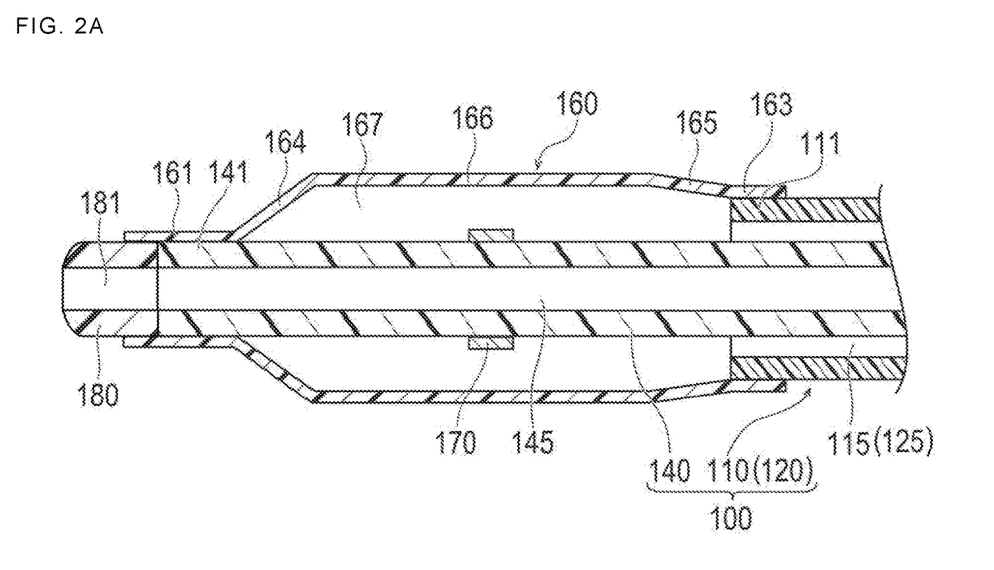
FIG. 2A is an enlarged cross-sectional view of a portion surrounded by a broken line portion 2A of FIG. 1.
Figure 2B:
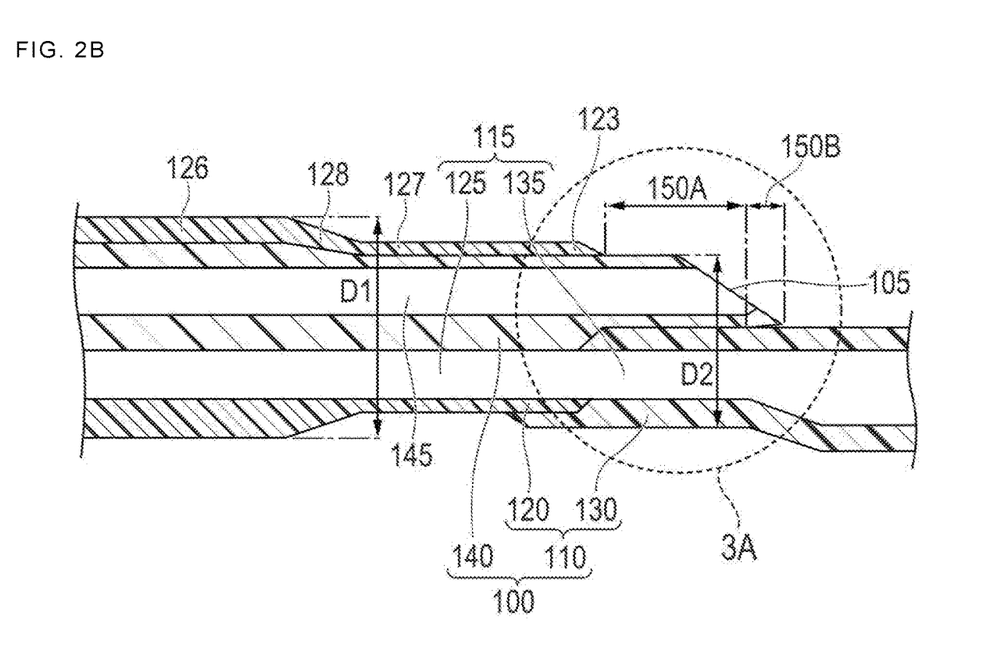
FIG. 2B is an enlarged cross-sectional view of a portion surrounded by a broken line portion 2B of FIG. 1.

As illustrated in FIGS. 2A and 2B, the shaft 100 has an outer shaft 110 including a lumen (inflation lumen) 115, and an inner shaft 140 including a lumen (guide wire lumen) 145 which is disposed in the lumen 115 of the outer shaft 110 and into which the guide wire 200 can be inserted.

As illustrated in FIGS. 1 and 2B, the shaft 100 has the proximal opening portion (equivalent to a "proximal opening portion of the inner shaft") 105 communicating with the lumen 145 of the inner shaft 140. The proximal opening portion 105 is formed in the vicinity of a proximal end of the inner shaft 140.

As illustrated in FIG. 2B, the outer shaft 110 has an outer distal shaft 120, and an outer proximal shaft 130 fixed to a proximal side of the outer distal shaft 120.

In accordance with an exemplary embodiment, the outer distal shaft 120 can be formed as a tubular member having a lumen 125 extending in the axial direction is formed. Similarly, the outer proximal shaft 130 is formed as a tubular member having a lumen 135 extending in the axial direction.

In accordance with an exemplary embodiment, the outer distal shaft 120 and the outer proximal shaft 130 can be integrally connected (i.e., heat-welded or heat-shrunk) to the inner shaft 140 in the vicinity of the proximal opening portion 105 of the shaft 100.

As illustrated in FIG. 2B, the lumen 125 of the outer distal shaft 120 communicates with the lumen 135 of the outer proximal shaft 130. In addition, in a state where the lumen 125 of the outer distal shaft 120 communicates with the lumen 135 of the outer proximal shaft 130, the lumen 125 and the lumen 135 form the lumen (inflation lumen) 115 communicating with an inflation space 167 of the balloon 160.

The outer distal shaft 120 and the outer proximal shaft 130 can be formed of, for example, polyolefin such as polyethylene, polypropylene, ethylene-propylene copolymer, or ethylene-vinyl acetate copolymer, thermoplastic resin such as soft polyvinyl chloride, any of various elastomers such as polyurethane elastomer, polyamide elastomer, and polyester elastomer, polyamide, or crystalline plastic such as polyamide, crystalline polyethylene, or crystalline polypropylene.

As illustrated in FIG. 2A, a distal side of the inner shaft 140 is disposed in the lumen 125 of the outer distal shaft 120. A certain range on the distal side of the inner shaft 140 is disposed protruding to a distal side of the outer distal shaft 120.

In addition, as illustrated in FIG. 2B, the inner shaft 140 is configured such that a proximal side of the inner shaft 140 is disposed on an outer surface of the outer proximal shaft 130. The proximal opening portion 105 which opens on an outer surface side of the outer proximal shaft 130 is formed on the proximal side of the inner shaft 140. Note that a first region 150A and a second region 150B which will be described later are formed on the proximal side of the inner shaft 140.

As illustrated in FIG. 2A, the inner shaft 140 has a distal member 180 disposed on the distal side. The distal member 180 has a lumen 181 into which the guide wire 200 can be inserted.

Since the inner shaft 140 includes the distal member 180 on the distal side, when a distal end of the balloon catheter 10 comes into contact with a body lumen (intravascular wall or the like), the distal end can be prevented from causing damages to a body organ. The distal member 180 can be formed of, for example, a flexible resin material. However, the material of the distal member 180 is not specifically limited if the distal member 180 can be fixed to the inner shaft 140.

As illustrated in FIG. 2A, the lumen 145 of the inner shaft 140 communicates with the lumen 181 of the distal member 180 on the distal side of the inner shaft 140. In addition, as illustrated in FIG. 2B, the lumen 145 of the inner shaft 140 communicates with the proximal opening portion 105 on the proximal side of the inner shaft 140.

In accordance with an exemplary embodiment, the inner shaft 140 can be formed of, for example, the same materials as the materials used for the materials of the outer shaft 110.

As illustrated in FIG. 2A, the balloon 160 has a distal portion 161 fixed to a distal portion of the inner shaft 140; a proximal portion 163 fixed to a distal portion of the outer shaft 110 (distal portion of the outer distal shaft 120); and an intermediate portion 166 that forms a maximum outer diameter portion formed between the distal portion 161 of the balloon 160 and the proximal portion 163 of the balloon 160. In addition, the balloon 160 has a distal side tapered portion 164 formed between the distal portion 161 of the balloon 160 and the intermediate portion 166 of the balloon 160, and a proximal side tapered portion 165 formed between the proximal portion 163 of the balloon 160 and the intermediate portion 166 of the balloon 160.

In accordance with an exemplary embodiment, the balloon 160 has the inflation space 167 formed between the balloon 160 and an outer circumferential surface of the shaft 100 and communicating with the lumen 115 of the outer shaft 110. For example, if a fluid flows into the inflation space 167, the balloon 160 can be inflated in a radial direction of the balloon 160 which intersects the axial direction.

In accordance with an exemplary embodiment, the balloon 160 can be formed of, for example, polyolefin such as polyethylene, polypropylene, or ethylene-propylene copolymer, polyester such as polyethylene terephthalate, thermoplastic resin such as polyvinyl chloride, ethylene-vinyl acetate copolymer, cross-linked ethylene-vinyl acetate copolymer, or polyurethane, polyamide, polyamide elastomer, polystyrene elastomer, silicone rubber, or latex rubber.

As illustrated in FIG. 2A, the inner shaft 140 has a contrast marker 170 indicating substantially an axially central position of the intermediate portion 166 of the balloon 160. The contrast marker 170 can be formed of, for example, metal such as platinum, gold, silver, iridium, titanium, or tungsten, or alloys of metals disclosed. Note that the contrast marker 170 may be disposed at a position indicating a boundary portion between the distal side tapered portion 164 and the intermediate portion 166 in the inner shaft 140, or at a position indicating a boundary portion between the proximal side tapered portion 165 and the intermediate portion 166 in the inner shaft 140.

As illustrated in FIG. 1, the hub 190 has a port 191 that can be liquid-tightly and air-tightly connected to a supply device (not illustrated), for example, a pressure application instrument, such as an indeflator for supplying a fluid (for example, contrast agent or saline solution). For example, the port 191 of the hub 190 can be configured as a luer taper, which can be configured such that a tube or the like can be connected to and detached from the port 191 of the hub 190.

Subsequently, the inner shaft 140 will be described in detail.

Figure 3:
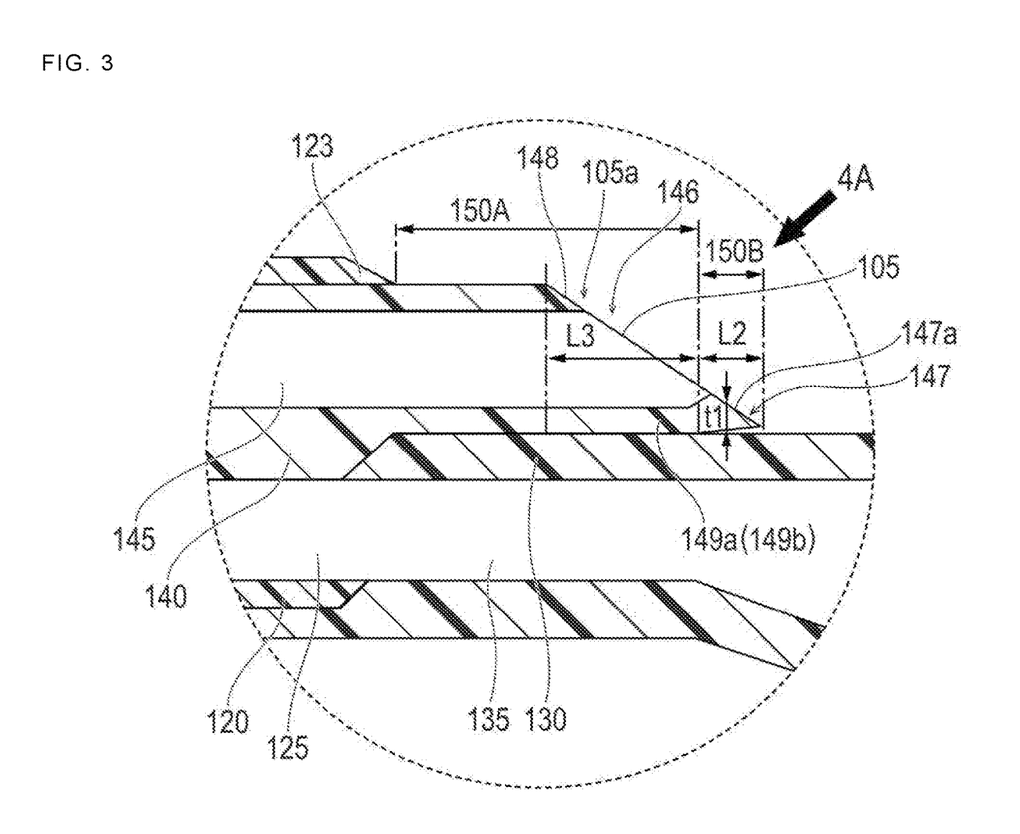
FIG. 3 is an enlarged view illustrating a portion surrounded by a broken line portion 3A of FIG. 2B.

As illustrated in FIG. 2B and FIG. 3, the inner shaft 140 has the first region 150A, and the second region 150B disposed on a proximal side of the first region 150A. Note that FIG. 3 is an enlarged cross-sectional view (enlarged cross-sectional view of the inner shaft 140 in the axial direction) of a portion 3A surrounded by the broken line illustrated in FIG. 2B.

As illustrated in FIG. 3, the first region 150A is a region where the inner shaft 140 and the outer proximal shaft 130 are fixed (for example, heat-welded or heat-shrunk) together in a range from a proximal end 123 of the outer distal shaft 120 to the proximal opening portion 105 of the inner shaft 140 (in an axial range from the proximal end 123 of the outer distal shaft 120 to a proximal end of the proximal opening portion 105 of the inner shaft 140). In addition, the second region 150B is a region where the inner shaft 140 and the outer proximal shaft 130 are not fixed (heat-welded or heat-shrunk) together in the range from the proximal end 123 of the outer distal shaft 120 to the proximal opening portion 105 of the inner shaft 140.

As will be described later in a method for manufacturing the shaft 100, the first region 150A is formed in a region where a heat shrinkable tube 400 is disposed in the inner shaft 140 when heat-welding (heat-shrinking) together the shafts 120, 130, and 140. In addition, the second region 150B is formed in a region located farther to the proximal side than the region where the heat shrinkable tube 400 is disposed in the inner shaft 140 (refer to FIGS. 6B and 6C).

As illustrated in FIG. 3, the inner shaft 140 has an inclined portion 146 inclined from the first region 150A to the second region 150B. In addition, the proximal opening portion 105 of the inner shaft 140 can be formed in the inclined portion 146.

As illustrated in FIG. 3, in an axial cross-section of the inner shaft 140, the proximal opening portion 105 of the inner shaft 140 is inclined from the proximal side of the inner shaft 140 to the distal side. Since the proximal opening portion 105 is formed in the inclined portion 146, the proximal opening portion 105 and the inclined portion 146 are disposed on the same plane.

Note that the inclined angle of the inclined portion 146 inclined with respect to the axial direction is not specifically limited. In addition, the proximal opening portion 105 may not be formed in the inclined portion 146, but instead, for example, may be formed in such a way that the proximal opening portion 105 opens substantially perpendicular to the axial direction of the inner shaft 140.

Figure 4:
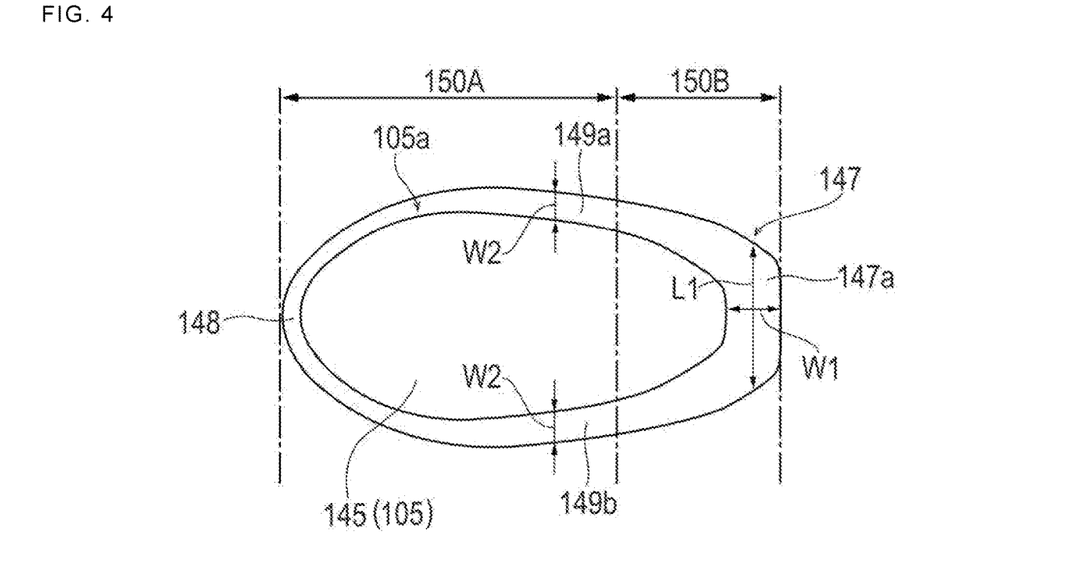
FIG. 4 is an arrow view of an inner shaft taken in the direction of an arrow head 4A of FIG. 3.

As illustrated in FIGS. 3 and 4, the proximal opening portion 105 of the inner shaft 140 has a non-fixed portion 147 at the position of the second region 150B facing the outer surface of the outer proximal shaft 130. Note that FIG. 4 is an arrow view of the inner shaft 140 taken in the direction of an arrow head 4A illustrated in FIG. 3.

In accordance with an exemplary embodiment, the non-fixed portion 147 is formed in a proximal portion of a peripheral edge portion 105a of the proximal opening portion 105. In addition, the non-fixed portion 147 forms a flat portion 147a in the peripheral edge portion 105a of the proximal opening portion 105.

In the arrow view illustrated in FIG. 4, the flat portion 147a is formed at a proximal end of the peripheral edge portion 105a of the proximal opening portion 105 and in the vicinity of the proximal end such that the flat portion 147a is continuous with an inner surface of the inner shaft 140. The flat portion 147a is formed such that a width W1 of the flat portion 147a along the axial direction of the inner shaft 140 is longer than the width of an opposite portion 148 (which will be described later) (region formed at a distal end of the peripheral edge portion 105a of the proximal opening portion 105 and in the vicinity of the distal end), and a distance L1 of the flat portion 147a in a direction perpendicular to the axial direction of the inner shaft 140 is longer than the distance of the opposite portion 148 (which will be described later) (region formed at the distal end of the peripheral edge portion 105a of the proximal opening portion 105 and in the vicinity of the distal end). Therefore, since the flat portion 147a is formed in a region in the peripheral edge portion 105a of the proximal opening portion 105, in which the thickness of the inner shaft 140 is relatively large and the circumferential length of the inner shaft 140 is relatively long, even though the non-fixed portion 147 can be excessively bent due to being aligned with the guide wire inserted into the lumen 145 of the inner shaft 140, it is possible to restrain the non-fixed portion 147 from being bent and improve the operability of the guide wire operated by an operator. As will be described later, the flat portion 147a can be formed by adjusting a cut angle (cut direction) of the inner shaft 140 and cutting away the proximal end of the peripheral edge portion 105a of the proximal opening portion 105 when forming the proximal opening portion 105 and the inclined portion 146 of the inner shaft 140 (refer to FIG. 7).

As illustrated in FIG. 3, the flat portion 147a is formed such that a thickness t1 of the flat portion 147a decreases from the distal side toward the proximal side in the axial direction. In accordance with an exemplary embodiment, the thickness t1 of the flat portion 147a decreases gradually toward the proximal side along an inclined direction of the inclined portion 146, and becomes minimum at the proximal end of the peripheral edge portion 105a of the proximal opening portion 105.

As illustrated in FIG. 4, the proximal opening portion 105 includes the opposite portion 148 that is opposite to the non-fixed portion 147 in a state where the lumen 145 (or the proximal opening portion 105) of the inner shaft 140 is interposed between the opposite portion 148 and the non-fixed portion 147, and a pair of side wall portions 149a and 149b at positions intersecting a direction (i.e., rightward and leftward direction as shown in FIG. 4) along which the non-fixed portion 147 is connected to the opposite portion 148.

As illustrated in FIGS. 3 and 4, in the proximal opening portion 105, the thickness of each of the side wall portions 149a and 149b increases from the opposite portion 148 toward the flat portion 147a. For this reason, as illustrated in FIG. 4, in the proximal opening portion 105, a width W2 (refer to FIG. 4) of each of the side wall portions 149a and 149b increases from the opposite portion 148 toward the flat portion 147a.

As will be described later, the opposite portion 148 is formed in a portion covered with the heat shrinkable tube 400 when the shafts 120, 130, and 140 are joined together (by heat-welding or heat-shrinking). In addition, when the shafts 120, 130, and 140 are to be heat-shrunk (or joined) together, at least part of each of the side wall portions 149a and 149b is disposed closer to the proximal side than a proximal end 403 of the heat shrinkable tube 400 (refer to FIG. 6C). Herein, heat applied to the heat shrinkable tube 400 can affect a certain range closer to the proximal side than the proximal end 403 of the heat shrinkable tube 400. For this reason, a portion of the inner shaft 140 in which each of the side wall portions 149a and 149b is formed has a thickness after heat-welding (or heat-shrinking) and the width W2 which increase from the distal side relatively highly affected by heat applied to the heat shrinkable tube 400 toward the proximal side not much affected by heat. Therefore, as illustrated in FIGS. 3 and 4, the proximal opening portion 105 is formed such that the thickness and the width W2 increase from the opposite portion 148 toward the flat portion 147a.

As illustrated in FIG. 3, in an axial cross-section of the inner shaft 140, an axial length L2 of the second region 150B of the inclined portion 146 is shorter than an axial length L3 of the first region 150A of the inclined portion 146.

In accordance with an exemplary embodiment, the axial length of the second region 150B of the inclined portion 146 can be, for example, from 0.1 mm to 0.5 mm, and the axial length of the first region 150A of the inclined portion 146 can be, for example, from 0.4 mm to 2.5 mm.

As illustrated in FIG. 2, the outer distal shaft 120 has a large diameter portion 126 formed having a predetermined outer diameter D1. In addition, an outer diameter (maximum outer diameter formed by the outer shaft 110 and the inner shaft 140 at a portion corresponding to the first region 150A and the second region 150B) D2 formed by the outer shaft 110 and the inner shaft 140 at a portion corresponding to the first region 150A and the second region 150B is smaller than the outer diameter D1 of the large diameter portion 126.

As will be described later, when the shafts 120, 130, and 140 are joined (or heat-welded or heat-shrunk) together (refer to FIG. 6B), a predetermined range of the shafts 120, 130, and 140 are covered with the heat shrinkable tube 400. If heat is applied to the shafts 120, 130, and 140 in this state, a range of the shafts 120, 130, and 140 covered with the heat shrinkable tube 400 shrink radially inward (in a direction toward the inside of the shaft 100). At that time, a range of the outer distal shaft 120 which is not affected by heat maintains a constant outer diameter before and after heating (i.e., heat-welding or heat-shrinking). As illustrated in FIG. 2B, a portion of the outer distal shaft 120, which maintains the constant outer diameter before and after heating (heat-welding or heat-shrinking), forms the large diameter portion 126. A portion of the outer distal shaft 120 which has an outer diameter decreased after the shafts 120, 130, and 140 are heat-welded (or heat-shrunk) together, for example, the portion covered with the heat shrinkable tube 400 when the shafts 120, 130, and 140 are being heat-welded (or heat-shrunk) together forms a small diameter portion 127 having an outer diameter smaller than the outer diameter of the large diameter portion 126. In addition, a boundary portion 128 is formed between the large diameter portion 126 and the small diameter portion 127, and heat applied to the heat shrinkable tube 400 causes the outer diameter of the boundary portion 128 to increase gradually from the small diameter portion 127 toward the large diameter portion 126.

Subsequently, the method for manufacturing the shaft (medical elongated body) 100 will be described with reference to FIGS. 5A to 7.

Firstly, a worker manufacturing the shaft 100 supplies (prepares) the outer distal shaft 120, the outer proximal shaft 130, the inner shaft 140, a first mandrel 310 to be disposed in the lumen 145 of the inner shaft 140, and a second mandrel 320 to be disposed in the lumen 125 of the outer distal shaft 120 and the lumen 135 of the outer proximal shaft 130.

As the outer distal shaft 120, for example, the worker prepares a tubular member having an outer diameter and an inner diameter which are substantially constant in an axial direction. In addition, as the outer proximal shaft 130, for example, the worker prepares a tubular member, the distal end of which is obliquely inclined from a distal side toward a proximal side, and in which a portion other than the distal end has an outer diameter and an inner diameter which are substantially constant in an axial direction. In addition, as the inner shaft 140, for example, the worker prepares a tubular member having an outer diameter and an inner diameter which are substantially constant in an axial direction, and in which an opening portion 143a is formed in a proximal end 143 (refer to FIG. 5C for an example of the shape of each of the shafts 120, 130, and 140).

As each of the first mandrel 310 and the second mandrel 320, for example, the worker may use a mandrel that extends substantially straight in an axial direction.

Figure 5A:
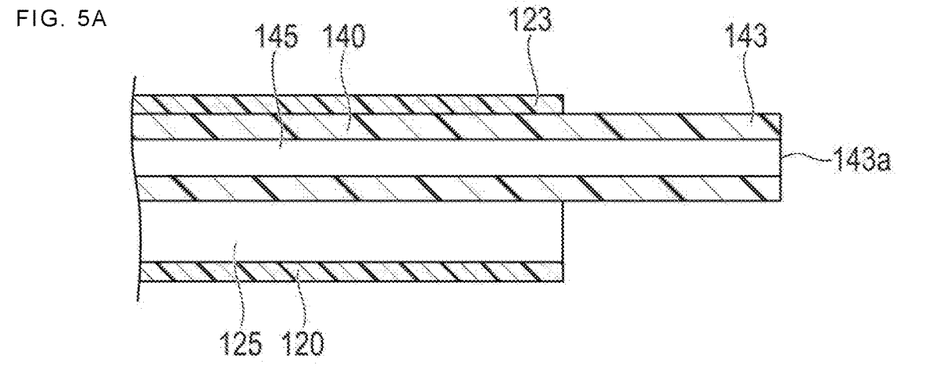
FIG. 5A is a cross-sectional view illustrating a state where the inner shaft is disposed in an axial direction while being stacked on an outer distal shaft.

As illustrated in FIG. 5A, the worker disposes the inner shaft 140 in the lumen 125 of the outer distal shaft 120. At that time, the worker disposes the inner shaft 140 such that the proximal side of the inner shaft 140 protrudes by a predetermined range from the proximal end 123 of the outer distal shaft 120.

Figure 5B:
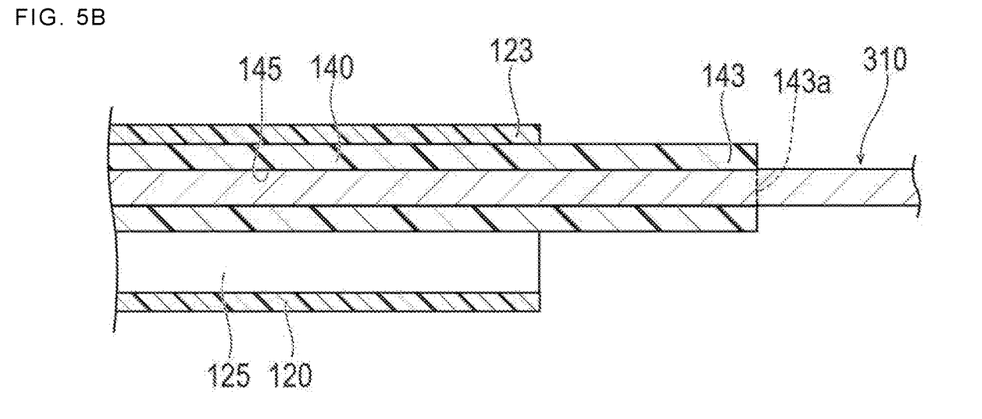
FIG. 5B is a cross-sectional view illustrating a state where a first mandrel is inserted into the inner shaft.

Subsequently, as illustrated in FIG. 5B, the worker inserts the first mandrel 310 into the lumen 145 of the inner shaft 140. The first mandrel 310 is disposed such that a proximal side of the first mandrel 310 protrudes from the opening portion 143a of the inner shaft 140.

Figure 5C:
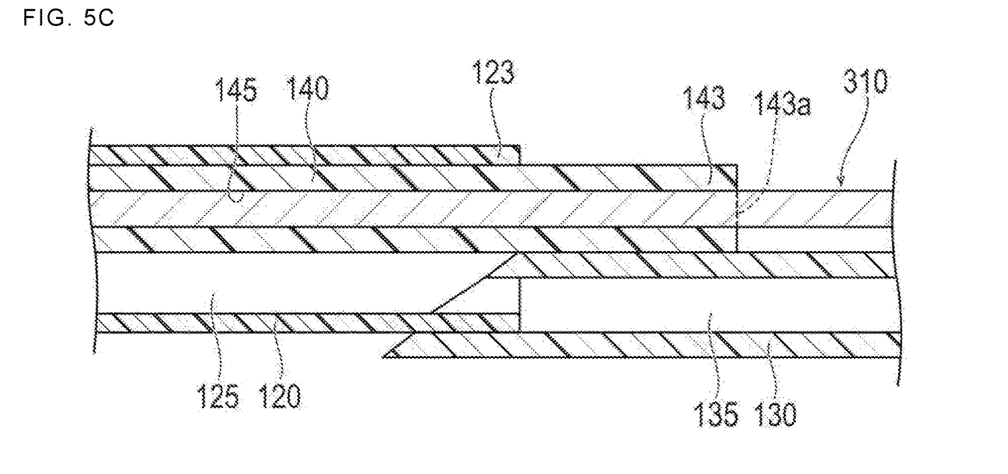
FIG. 5C is a cross-sectional view illustrating a state where an outer proximal shaft is inserted into a lumen of the outer distal shaft.

Subsequently, as illustrated in FIG. 5C, the worker disposes the outer proximal shaft 130 such that the distal side of the inner shaft 140 is disposed in the lumen 125 of the outer distal shaft 120 and the proximal side of the inner shaft 140 is disposed on the outer surface of the outer proximal shaft 130.

Figure 6A:
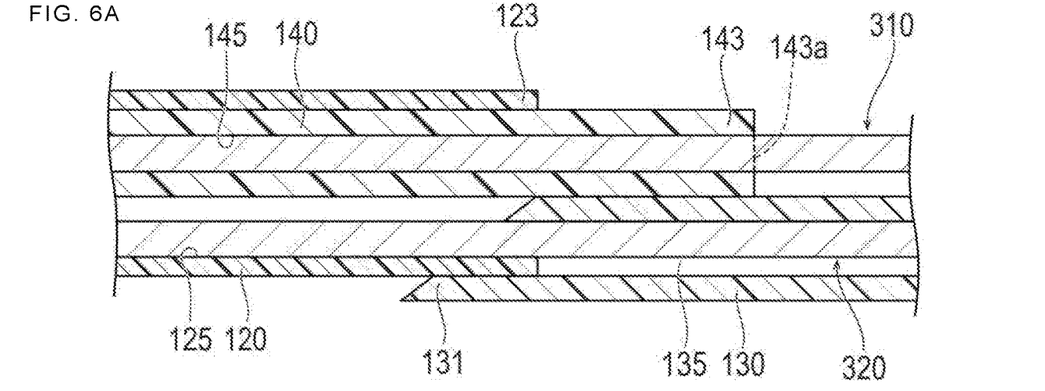
FIG. 6A is a cross-sectional view illustrating a state where a second mandrel is inserted into the lumen of the outer distal shaft and a lumen of the outer proximal shaft.

Subsequently, as illustrated in FIG. 6A, the worker inserts the second mandrel 320 into the lumen 125 of the outer distal shaft 120 and the lumen 135 of the outer proximal shaft 130.

Note that the worker may perform, in random order, the operation of disposing the inner shaft 140 in the lumen 125 of the outer distal shaft 120, the operation of disposing the first mandrel 310 in the inner shaft 140, the operation of disposing the outer proximal shaft 130 in the outer distal shaft 120, and the operation of inserting the second mandrel 320 into the lumen 125 of the outer distal shaft 120 and the lumen 135 of the outer proximal shaft 130.

Figure 6B:
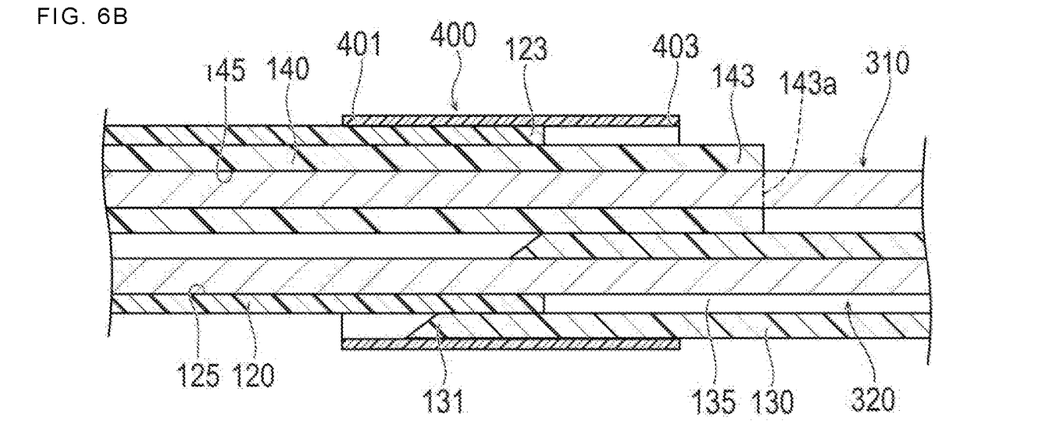
FIG. 6B is a cross-sectional view illustrating a state where a heat shrinkable tube is disposed.

Subsequently, as illustrated in FIG. 6B, the worker disposes the heat shrinkable tube 400 so as to cover the proximal end 123 of the outer distal shaft 120, a distal end 131 of the outer proximal shaft 130, and the inner shaft 140. At that time, the worker disposes the proximal end 403 of the heat shrinkable tube 400 closer to the distal side in the axial direction than the proximal end 143 of the inner shaft 140, and disposes a distal end 401 of the heat shrinkable tube 400 closer to the distal side in the axial direction than the proximal end 123 of the outer distal shaft 120 and the distal end 131 of the outer proximal shaft 130.

In accordance with an exemplary embodiment, the heat shrinkable tube 400, for example, can be a hollow cylindrical member formed of polyolefin or the like.

Subsequently, the worker causes the heat shrinkable tube 400 to shrink by applying heat to the heat shrinkable tube 400, and heat-shrinks together the outer distal shaft 120, the outer proximal shaft 130, and the inner shaft 140 in a state where the proximal end 143 of the inner shaft 140 is not shrunk by the heat shrinkable tube 400. If the heat shrinkable tube 400 is heated, the heat shrinkable tube 400 shrinks and is deformed such that the inner diameter of the heat shrinkable tube 400 after being heated becomes smaller than the inner diameter of the heat shrinkable tube 400 before being heated.

Figure 6C:
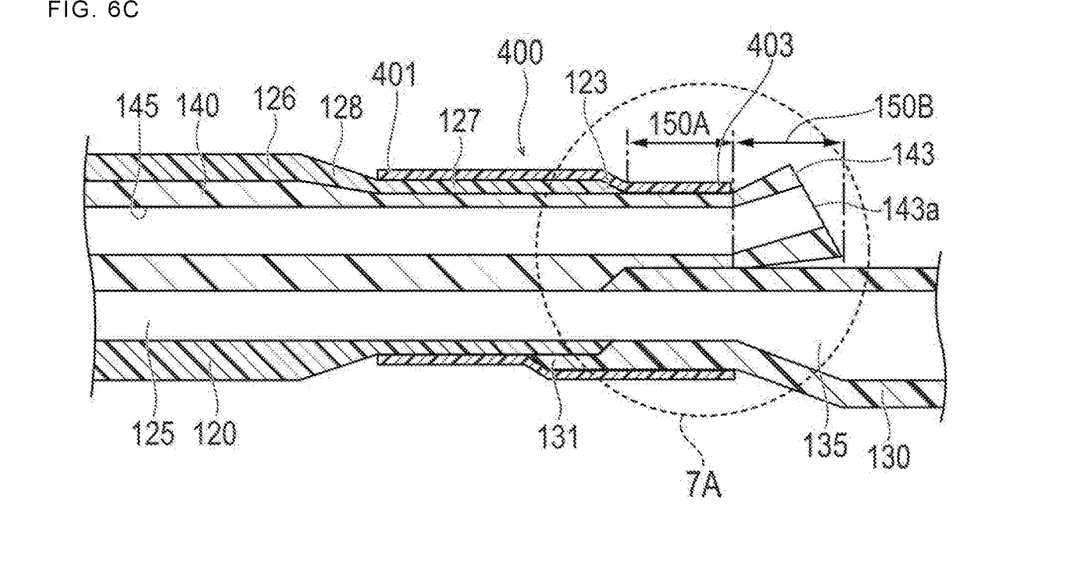
FIG. 6C is a cross-sectional view illustrating the outer distal shaft, the outer proximal shaft, and the inner shaft after being heat-welded (or heat-shrunk) together.

The worker heat-welds (heat-shrink) together the shafts 120, 130, and 140 by causing the heat shrinkable tube 400 to shrink, so that as illustrated in FIG. 6C, the first region 150A and the second region 150B are formed in the inner shaft 140.

As illustrated in FIG. 6C, since the first region 150A positioned closer to the proximal side than the proximal end 403 of the heat shrinkable tube 400 is affected by heat applied to the heat shrinkable tube 400 when the shafts 120, 130, and 140 are being heat-welded together, the first region 150A has a cross-sectional shape, the thickness of which increases gradually from the distal side toward the proximal side. In addition, since the vicinity of the proximal end 143 of the inner shaft 140 is minimally affected by heat applied to the heat shrinkable tube 400, the thickness can be maintained substantially constant before and after heat-welding.

Similar to the inner shaft 140, since a portion of the outer proximal shaft 130 positioned in the vicinity of the proximal end 403 of the heat shrinkable tube 400 can be affected by heat applied to the heat shrinkable tube 400, the outer proximal shaft 130 has such cross-sectional shape that the thickness of the portion increases from the distal side toward the proximal side. In addition, the thickness of a portion of the outer proximal shaft 130, which is spaced apart by a predetermined distance from the proximal end 403 of the heat shrinkable tube 400 toward the proximal side, can be maintained substantially constant before and after heat-welding (heat-shrinking).

As illustrated in FIG. 6C, after heat-welding (heat-shrinking), the small diameter portion 127 can be formed in a portion of the outer distal shaft 120 which is covered with the heat shrinkable tube 400, the boundary portion 128 is formed in a portion (positioned closer to the distal side than the small diameter portion 127) of the outer distal shaft 120, which is not covered with the heat shrinkable tube 400, and the large diameter portion 126 is formed on a distal side of the boundary portion 128.

After the shafts 120, 130, and 140 are heat-welded (heat-shrunk) together, the worker pulls the first mandrel 310 out from the lumen 145 of the inner shaft 140. For example, in random order, the worker may pull the second mandrel 320 out from the lumen 125 of the outer distal shaft 120 and the lumen 135 of the outer proximal shaft 130, and pulling the first mandrel 310 out from the lumen 145 of the inner shaft 140. Note that in the illustrated example, the worker pulls out the mandrels 310 and 320 after heat-welding (heat-shrinking).

Figure 7:
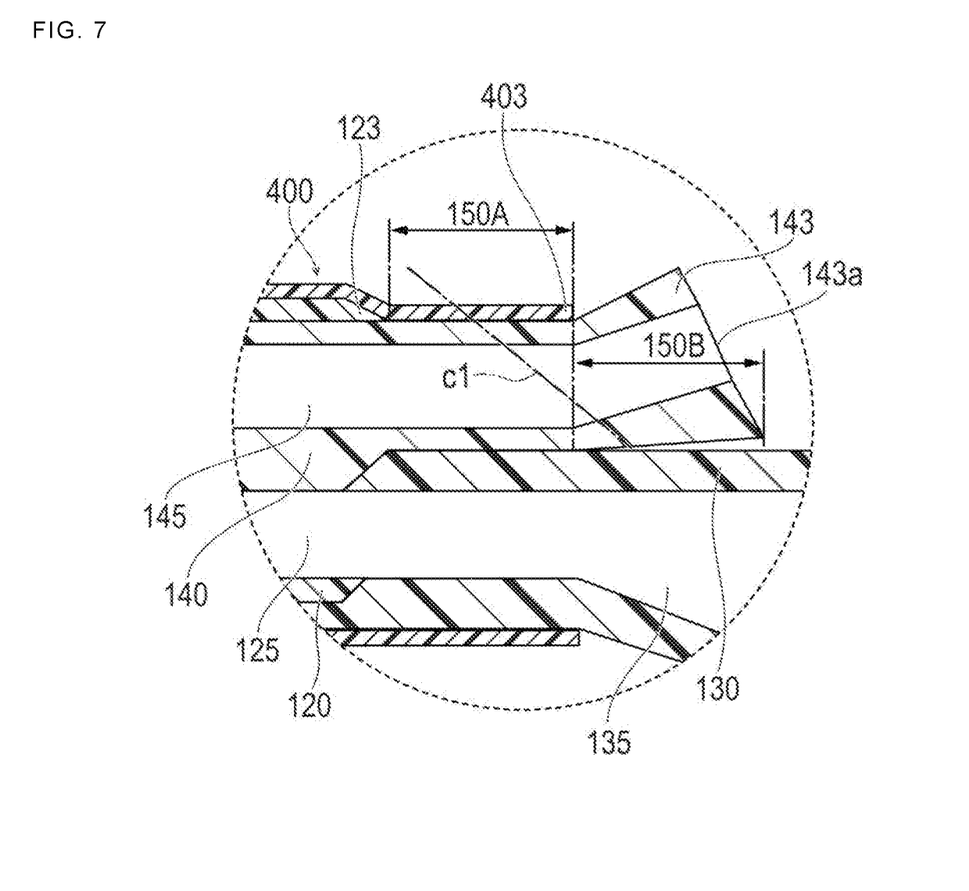
FIG. 7 is an enlarged cross-sectional view of a portion surrounded by a broken line portion 7A of FIG. 6C, and a view for describing a cut position of the inner shaft.

Subsequently, as illustrated in FIG. 7, the worker obliquely cuts a proximal portion (certain range on the proximal side containing the proximal end 143) of the inner shaft 140 across the first region 150A of the inner shaft 140 and the second region 1506 of the inner shaft 140 (example of a cut position illustrated by a broken line c1 of FIG. 7). Note that before obliquely cutting the proximal portion of the inner shaft 140 (certain range on the proximal side containing the proximal end 143) across the first region 150A of the inner shaft 140 and the second region 1506 of the inner shaft 140, the worker pulls out the heat shrinkable tube 400. FIG. 7 is an enlarged cross-sectional view of a portion surrounded by a broken line portion 7A of FIG. 6C, and a view for describing the cut position.

Since the worker cuts the inner shaft 140 as described above, the inclined portion 146 inclined from the first region 150A of the inner shaft 140 toward the second region 150B of the inner shaft 140 is formed (refer to FIG. 3). At that time, the worker cuts the inner shaft 140 such that the axial length L2 of the second region 1506 of the inclined portion 146 is shorter than the axial length L3 of the first region 150A of the inclined portion 146 (refer to FIG. 3).

Since the worker cuts the inner shaft 140 as described above, the proximal opening portion 105 is formed in the inner shaft 140 (refer to FIG. 3). In addition, at that time, the worker forms the non-fixed portion 147, which is not fixed to the outer proximal shaft 130, in the peripheral edge portion 105a of the proximal opening portion 105 of the inner shaft 140 (refer to FIG. 4).

In addition, since the worker cuts the inner shaft 140 as described above, as illustrated in FIG. 4, the flat portion 147a is formed in the non-fixed portion 147 positioned in the second region 150B, the opposite portion 148 is formed in the peripheral edge portion 105a of the proximal opening portion 105 at a position opposite to the non-fixed portion 147 in a state where the lumen 145 is interposed between the opposite portion 148 and the non-fixed portion 147, and the side wall portions 149a and 149b are formed connecting the opposite portion 148 to the non-fixed portion 147.

In accordance with an exemplary embodiment, each of the side wall portions 149a and 149b is formed across the first region 150A and the second region 1506 of the inner shaft 140. In addition, each of the side wall portions 149a and 149b of the proximal opening portion 105 of the inner shaft 140 has the thickness and the width W2 illustrated in FIG. 4 which increase from the opposite portion 148 toward the flat portion 147a.

The inner shaft 140 can be cut with a tool provided with a blade capable of cutting the inner shaft 140.

Note that the cut position or the cut angle (cut direction) of the inner shaft 140 is not specifically limited. In the embodiment, the inner shaft 140 is cut at a predetermined position where the flat portion 147a is formed in the peripheral edge portion 105a of the proximal opening portion 105, and at a predetermined angle. However, for example, the worker may cut the inner shaft 140 substantially perpendicular to the axial direction of the inner shaft 140 such that the proximal opening portion 105 of the inner shaft 140 does not have an inclined cross-sectional shape.

In accordance with an exemplary embodiment, the worker may execute each step described above to manufacture the shaft 100 including the inner shaft 140 in which the first region 150A and the second region 150B are formed, and the outer shaft 110 formed by the outer distal shaft 120 and the outer proximal shaft 130.

Subsequently, effects of the balloon catheter 10 and effects of the method for manufacturing the shaft 100 according to the embodiment will be described.

The balloon catheter 10 according to the embodiment includes the inner shaft 140; the outer shaft 110 covering part of the inner shaft 140; and the balloon 160 fixed to the inner shaft 140 and the outer shaft 110. The outer shaft 110 has the outer distal shaft 120 having the lumen 125, and the outer proximal shaft 130 fixed to the proximal side of the outer distal shaft 120 and having the lumen 135 communicating with the lumen 125 of the outer distal shaft 120. In addition, the distal side of the inner shaft 140 is disposed in the lumen 125 of the outer distal shaft 120, and the proximal side of the inner shaft 140 is disposed on the outer surface of the outer proximal shaft 130. The inner shaft 140 forms the proximal opening portion 105 which opens on the outer surface side of the outer proximal shaft 130. The inner shaft 140 has the first region 150A and the second region 150B disposed on the proximal side of the first region 150A, in the range from the proximal end 123 of the outer distal shaft 120 disposed on the outer surface of the outer proximal shaft 130 to the proximal opening portion 105 of the inner shaft 140. In accordance with an exemplary embodiment, the first region 150A is fixed to the outer surface of the outer proximal shaft 130, and the second region 150B is not fixed to the outer surface of the outer proximal shaft 130.

Since the second region 150B positioned on the proximal side of the inner shaft 140 is not fixed to the outer surface of the outer proximal shaft 130, for example, when the guide wire 200 is being taken out from the proximal opening portion (guide wire port) 105 of the inner shaft 140, the foregoing configuration of the balloon catheter 10 can help prevent stress from being concentrated in the vicinity of the proximal opening portion 105. In the balloon catheter 10, therefore, the inner shaft 140 can be prevented from being fractured, and deterioration in the operability of the guide wire 200 can be prevented, which would otherwise be induced by fracturing of the inner shaft 140. In addition, since the second region 150B positioned on the proximal side of the inner shaft 140 is not fixed to the outer surface of the outer proximal shaft 130, when the balloon catheter 10 is delivered to a body lumen such as a curved blood vessel, the balloon catheter 10 is rather easily deformed such that the second region 150B follows the guide wire 200. Therefore, in the balloon catheter 10, the followability of the inner shaft 140 with respect to the guide wire 200 can be improved.

In addition, the inner shaft 140 of the balloon catheter 10 has the inclined portion 146 inclined from the first region 150A toward the second region 150B. The proximal opening portion 105 is formed in the inclined portion 146. For this reason, in the balloon catheter 10, the proximal opening portion 105 can be formed having a larger opening area compared to when the proximal opening portion 105 of the inner shaft 140 opens perpendicular to the axial direction of the inner shaft 140. Therefore, an operator can rather easily remove the guide wire 200 through the proximal opening portion 105 of the balloon catheter 10.

In addition, the proximal opening portion 105 of the balloon catheter 10 has the non-fixed portion 147 at the position of the second region 150B facing the outer surface of the outer proximal shaft 130. The non-fixed portion 147 forms the flat portion 147a in the peripheral edge portion 105a of the proximal opening portion 105. For this reason, the flat portion 147a can help improve the kink resistance of the non-fixed portion 147. Therefore, even though the non-fixed portion 147 is excessively bent when aligned with the guide wire 200 inserted into the lumen 145 of the inner shaft 140, bending of the non-fixed portion 147 can be limited in the balloon catheter 10. For this reason, when the guide wire 200 is taken out through the proximal opening portion 105 of the inner shaft 140, the balloon catheter 10 can prevent a coil portion or the like of the guide wire 200 from being caught at the proximal end of the proximal opening portion 105. Therefore, the operator can rather easily and smoothly take the guide wire 200 out from the proximal opening portion 105 of the inner shaft 140.

In addition, the thickness of the flat portion 147a of the inner shaft 140 of the balloon catheter 10 decreases from the distal side toward the proximal side. In such configuration, the inner shaft 140 is fixed to the outer shaft 110 at a position closer to the distal side than the portion of the inner shaft 140 in which the flat portion 147a is formed. Namely, in the inner shaft 140, a proximal end (portion having the smallest thickness in the peripheral edge portion 105a of the proximal opening portion 105) of the flat portion 147a formed in the peripheral edge portion 105a of the proximal opening portion 105 of the inner shaft 140 is not fixed to the outer shaft 110. In the inner shaft 140, therefore, stress can be prevented from being concentrated at the proximal end of the flat portion 147a, and the occurrence of fracture can be prevented, which would otherwise be induced by stress concentrated on a portion of the inner shaft 140 which is positioned closer to the distal side than the flat portion 147a and has a relatively large thickness.

In addition, the proximal opening portion 105 of the inner shaft 140 of the balloon catheter 10 includes the opposite portion 148 that is opposite to the non-fixed portion 147 in a state where the lumen 145 of the inner shaft 140 is interposed between the opposite portion 148 and the non-fixed portion 147, and the side wall portions 149a and 149b formed at the positions intersecting the direction along which the non-fixed portion 147 is connected to the opposite portion 148. In accordance with an exemplary embodiment, the thickness of each of the side wall portions 149a and 149b increases from the opposite portion 148 toward the flat portion 147a.

In the balloon catheter 10 with the foregoing configuration, the thickness of each of the side wall portions 149a and 149b increases toward a proximal side of the peripheral edge portion 105a of the proximal opening portion 105. For this reason, in the balloon catheter 10, it is possible to reinforce the peripheral edge portion 105a of the proximal opening portion 105 of the inner shaft 140 by increasing the thickness of a portion of each of the side wall portions 149a and 149b in a region, which is positioned closer to the distal side than the non-fixed portion 147 of the inner shaft 140. Therefore, when stress is concentrated on the portion of each of the side wall portions 149a and 149b of the inner shaft 140, which is positioned closer to the distal side than the non-fixed portion 147, the balloon catheter 10 can help prevent the inner shaft 140 from being fractured in the vicinity of the peripheral edge portion 105a of the proximal opening portion 105. Note that if the proximal opening portion 105 is formed by the inclined portion 146, a cross section of the proximal portion of the inner shaft 140 which is perpendicular to the axial direction of the inner shaft 140 has an area decreasing from the distal side toward the proximal side. For this reason, in the balloon catheter 10, the opening area of the proximal opening portion 105 can be increased and the peripheral edge portion 105a of the proximal opening portion 105 of the inner shaft 140 can be reinforced by increasing the thickness of the portion of each of the side wall portions 149a and 149b, which is closer to the distal side than the non-fixed portion 147 of the inner shaft 140.

In addition, in the axial cross-section of the inner shaft 140, the axial length of the second region 150B of the inclined portion 146 of the balloon catheter 10 can be shorter than the axial length of the first region 150A of the inclined portion 146.

In the balloon catheter 10 with the foregoing configuration, in a large range of the inclined portion 146, the inner shaft 140 is in contact with the outer shaft 110 in the axial direction. For this reason, the balloon catheter 10 can have an increased fixing force between the inner shaft 140 and the outer shaft 110 in the inclined portion 146, and reduce the concentration of stress on the peripheral edge portion 105a of the proximal opening portion 105 of the inner shaft 140 by virtue of the non-fixed portion 147. For example, when the guide wire 200 comes into contact with the opposite portion 148 of the inner shaft 140, the balloon catheter 10 can reduce the concentration of stress between the proximal portion of the inner shaft 140 and the outer proximal shaft 130 by virtue of the non-fixed portion 147. Therefore, when stress is concentrated in the vicinity of the proximal opening portion 105 of the inner shaft 140, the balloon catheter 10 can help prevent the inner shaft 140 or the outer proximal shaft 130 from being fractured in the vicinity of the proximal opening portion 105.

In addition, the outer distal shaft 120 of the balloon catheter 10 has the large diameter portion 126 formed having the predetermined outer diameter, and the outer diameter formed by the outer shaft 110 and the inner shaft 140 at the portion corresponding to the first region 150A and the second region 150B is smaller than the outer diameter of the large diameter portion 126.

When inserting the balloon catheter 10 into a body lumen such as a blood vessel, the operator or the like may insert another medical device (for example, a balloon catheter separate from the balloon catheter or a catheter device used in image diagnosis) together with the balloon catheter 10 using one catheter (well-known guiding catheter or the like). At that time, if the outer diameter of the vicinity of the proximal opening portion 105 of the balloon catheter 10 is rather large, the balloon catheter 10 may interfere with the other medical devices inside the catheter, and the relatively smooth movement of both may be interrupted. As described above, since the outer diameter formed by the outer shaft 110 and the inner shaft 140 at the portion corresponding to the first region 150A and the second region 150B is smaller than the outer diameter of the large diameter portion 126 of the outer distal shaft 120, the balloon catheter 10 can be prevented from interfering with the other medical device in a lumen of the catheter.

The method for manufacturing the shaft 100 according to the embodiment supplies the outer distal shaft 120, the outer proximal shaft 130, the inner shaft 140, the first mandrel 310 to be disposed in the lumen 145 of the inner shaft 140, and the second mandrel 320 to be disposed in the lumen 125 of the outer distal shaft 120 and the lumen 135 of the outer proximal shaft 130. In addition, in the manufacturing method, the inner shaft 140 is disposed in the lumen 125 of the outer distal shaft 120, the first mandrel 310 is inserted into the lumen 145 of the inner shaft 140, the outer proximal shaft 130 is disposed such that the distal side of the inner shaft 140 is disposed in the lumen 125 of the outer distal shaft 120 and the proximal side of the inner shaft 140 is disposed on the outer surface of the outer proximal shaft 130, the second mandrel 320 is inserted into the lumen 125 of the outer distal shaft 120 and the lumen 135 of the outer proximal shaft 130, the heat shrinkable tube 400 is disposed so as to cover the proximal end 123 of the outer distal shaft 120, the distal end 131 of the outer proximal shaft, and the inner shaft 140, and the proximal end 403 of the heat shrinkable tube 400 is positioned closer to the distal side than the proximal end 143 of the inner shaft 140. The manufacturing method contains joining (heat-welding) together the outer distal shaft 120, the outer proximal shaft 130, and the inner shaft 140 in a state where the heat shrinkable tube 400 is shrunk by applying heat to the heat shrinkable tube 400 and the proximal end 143 of the inner shaft 140 is not heat-welded by the heat shrinkable tube 400.

In the method for manufacturing the shaft 100, when the inner shaft 140 is being heat-welded (i.e., fixed) to the outer shaft 110, since the proximal end 143 of the inner shaft 140 is not welded (fixed) by the heat shrinkable tube 400, the proximal end 143 of the inner shaft 140 is not fixed to the outer surface of the outer proximal shaft 130. Therefore, for example, when the guide wire 200 is being taken out from the proximal opening portion 105 of the inner shaft 140, the shaft 100 manufactured by the manufacturing method can help prevent stress from being concentrated in the vicinity of the proximal end 143 of the inner shaft 140. In addition, when being delivered to a body lumen such as a curved blood vessel, the vicinity of the proximal end 143 of the inner shaft 140 can be rather easily deformed to follow the guide wire 200. In the shaft 100 manufactured by the manufacturing method, therefore, the inner shaft 140 can have an improved ability to follow the guide wire 200.

In addition, in the method for manufacturing the shaft 100, after the outer distal shaft 120, the outer proximal shaft 130, and the inner shaft 140 are heat-welded together, the inner shaft 140 has the first region 150A in which the inner shaft 140 is heat-welded to the outer proximal shaft 130, and the second region 150B which is disposed on the proximal side of the first region 150A and in which the inner shaft 140 is not heat-welded to the outer proximal shaft 130, in a range from the proximal end 123 of the outer distal shaft 120 disposed in an outer surface of the outer shaft 110 to the proximal end 143 of the inner shaft 140. The manufacturing method contains obliquely cutting the proximal portion of the inner shaft 140 across the first region 150A and the second region 150B to form the inclined portion 146 inclined from the first region 150A toward the second region 150B.

In the method for manufacturing the shaft 100, the proximal end 143 of the inner shaft 140 is obliquely cut across the first region 150A and the second region 150B to form the inclined portion 146 inclined from the first region 150A toward the second region 150B. Moreover, in the manufacturing method, the proximal opening portion 105 of the inner shaft 140 is formed across the first region 150A of the inner shaft 140 and the second region 150B of the inner shaft 140. In the shaft 100 manufactured by the manufacturing method, the opening area of the proximal opening portion 105 is larger compared to when the proximal opening portion 105 of the inner shaft 140 opens perpendicular to the axial direction of the inner shaft 140, and thus the operator can rather easily remove the guide wire 200 through the proximal opening portion 105 of the balloon catheter 10. In addition, since the proximal end of the proximal opening portion 105 is contained in the second region 150B where the inner shaft 140 is not fixed to the outer shaft 110, the shaft 100 can help prevent stress from being concentrated at the proximal end of the proximal opening portion 105 of the inner shaft 140. Therefore, the shaft 100 can help prevent the fracturing of the vicinity of the proximal opening portion 105 of the inner shaft 140, which would otherwise be induced by the concentration of stress.

In addition, the method for manufacturing the shaft 100 contains pulling the first mandrel 310 out from the lumen 145 of the inner shaft 140 before cutting the proximal portion of the inner shaft 140. For this reason, in the manufacturing method, when cutting the inner shaft 140, the first mandrel 310 can be prevented from interrupting the relatively smooth progress of the cutting operation. Therefore, a worker manufacturing the shaft 100 can rather easily cut the proximal portion of the inner shaft 140 into a predetermined shape across the first region 150A and the second region 150B.

In addition, in the method for manufacturing the shaft 100, when the inclined portion 146 inclined from the first region 150A toward the second region 150B is formed by cutting the proximal portion of the inner shaft 140, the inner shaft 140 is cut such that in the axial cross-section of the inner shaft 140, the axial length of the second region 1506 of the inclined portion 146 is shorter than the axial length of the first region 150A of the inclined portion 146.

In the shaft 100 manufactured by the method for manufacturing the shaft 100, in a large range of the first region 150A, the inclined portion 146 of the inner shaft 140 is in contact with the outer shaft 110 in the axial direction. For this reason, the balloon catheter 10 can have an increased fixing force between the inner shaft 140 and the outer shaft 110 in the inclined portion 146, and reduce the concentration of stress on the peripheral edge portion 105a of the proximal opening portion 105 of the inner shaft 140 by virtue of the non-fixed portion 147. For example, when the guide wire 200 comes into contact with the opposite portion 148 of the inner shaft 140, the balloon catheter 10 can help reduce the concentration of stress between the proximal portion of the inner shaft 140 and the outer proximal shaft 130 by virtue of the non-fixed portion 147. Therefore, when stress is concentrated in the vicinity of the proximal opening portion 105 of the inner shaft 140, the shaft 100 can help prevent the inner shaft 140 or the outer proximal shaft 130 from being fractured in the vicinity of the proximal opening portion 105.

The balloon catheter and the method for manufacturing a medical elongated body of the present disclosure have been described above according to the embodiment. However, various modifications based on the claims can be made to the present disclosure, and the present disclosure is not limited only to the content of the embodiment which has been described.

For example, appropriate changes can be made to the structure, the disposition of the members, and the like of the balloon catheter which have been described in the embodiment and the like. Additional members described with reference to the drawings can be omitted, and other additional members which have not been described can be appropriately used. Similarly, appropriate changes can be made also to each step of the method for manufacturing a medical elongated body, the manufacturing instruments used, and the like.

The detailed description above describes to a balloon catheter and a method for manufacturing a medical elongated body. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A balloon catheter comprising:
an inner shaft;
an outer shaft covering a part of the inner shaft;
a balloon fixed to the inner shaft and the outer shaft;
the outer shaft having an outer distal shaft having a lumen, and an outer proximal shaft fixed to a proximal side of the outer distal shaft and having a lumen communicating with the lumen of the outer distal shaft;
a distal side of the inner shaft is disposed in the lumen of the outer distal shaft, a proximal side of the inner shaft is disposed on an outer surface of the outer proximal shaft, and the inner shaft forms a proximal opening portion which opens on an outer surface side of the outer proximal shaft;
the inner shaft having a first region and a second region disposed on a proximal side of the first region, in a range from a proximal end of the outer distal shaft disposed on the outer surface of the outer proximal shaft to the proximal opening portion, and wherein the first region is fixed to the outer surface of the outer proximal shaft, and the second region is not fixed to the outer surface of the outer proximal shaft;
the proximal opening portion including a non-fixed portion at a position of the second region facing the outer surface of the outer proximal shaft, and the non-fixed portion forms a flat portion in a peripheral edge portion of the proximal opening portion; and
wherein the proximal opening portion includes an opposite portion that is opposite to the non-fixed portion in a state where a lumen of the inner shaft is interposed between the opposite portion and the non-fixed portion, and a side wall portion at a position intersecting a direction along which the non-fixed portion is connected to the opposite portion, and a thickness of the side wall portion increases from the opposite portion toward the flat portion.

2. The balloon catheter according to claim 1, wherein the inner shaft has an inclined portion inclined from the first region toward the second region, and the proximal opening portion is formed in the inclined portion.

3. The balloon catheter according to claim 2, wherein in an axial cross-section of the inner shaft, an axial length of the second region of the inclined portion is shorter than an axial length of the first region of the inclined portion.

4. The balloon catheter according to claim 1, wherein a thickness of the flat portion decreases from a distal side toward a proximal side.

5. The balloon catheter according to claim 1, wherein the outer distal shaft has a large diameter portion formed having a predetermined outer diameter, and an outer diameter formed by the outer shaft and the inner shaft at a portion corresponding to the first region and the second region is smaller than the outer diameter of the large diameter portion.

6. The balloon catheter according to claim 1, wherein a width of the flat portion along an axial direction of the inner shaft is longer than a width of the opposite portion along the axial direction, and a distance of the flat portion in a direction perpendicular to the axial direction of the inner shaft is longer than a distance of the opposite portion in the direction perpendicular to the axial direction of the inner shaft.

7. The balloon catheter according to claim 1, further comprising:

a contrast marker on the inner shaft, and wherein the contrast marker indicates an axially central position of an intermediate portion of the balloon.

8. A medical elongated body, comprising:

an inner shaft;

an outer shaft covering a part of the inner shaft;

the outer shaft having an outer distal shaft having a lumen, and an outer proximal shaft fixed to a proximal side of the outer distal shaft and having a lumen communicating with the lumen of the outer distal shaft;

a distal side of the inner shaft is disposed in the lumen of the outer distal shaft, a proximal side of the inner shaft is disposed on an outer surface of the outer proximal shaft, and the inner shaft having a proximal opening portion on an outer surface side of the outer proximal shaft;

the inner shaft on the proximal end having a first region and a second region, the second region being on a proximal side of the first region, and wherein the first region is joined to the outer surface of the outer proximal shaft, and the second region is not joined to the outer surface of the outer proximal shaft; and wherein the proximal opening portion includes an opposite portion that is opposite to a non-fixed portion of the proximal opening portion in a state where a lumen of the inner shaft is interposed between the opposite portion and the non-fixed portion, and a side wall portion at a position intersecting a direction along which the non-fixed portion is connected to the opposite portion, and a thickness of the side wall portion increases from the opposite portion toward a flat portion of a peripheral edge portion of the proximal opening portion.

9. The elongated medical body according to claim 8, wherein the inner shaft has an inclined portion inclined from the first region toward the second region, and the proximal opening portion is formed in the inclined portion.

10. The elongated medical body according to claim 9, wherein in an axial cross-section of the inner shaft, an axial length of the second region of the inclined portion is shorter than an axial length of the first region of the inclined portion.

11. The elongated medical body according to claim 8, wherein the proximal opening portion a includes the non-fixed portion at a position of the second region facing the outer surface of the outer proximal shaft, and the non-fixed portion forms the flat portion in the peripheral edge portion of the proximal opening portion.

12. The elongated medical body according to claim 11, wherein a thickness of the flat portion decreases from a distal side toward a proximal side.

13. The elongated medical body according to claim 8, wherein the outer distal shaft has a large diameter portion formed having a predetermined outer diameter, and an outer diameter formed by the outer shaft and the inner shaft at a portion corresponding to the first region and the second region is smaller than the outer diameter of the large diameter portion.

14. A method for manufacturing a medical elongated body, the method comprising:

supplying an outer distal shaft, an outer proximal shaft, an inner shaft, a first mandrel to be disposed in a lumen of the inner shaft, and a second mandrel to be disposed in a lumen of the outer distal shaft and a lumen of the outer proximal shaft;

disposing the inner shaft in the lumen of the outer distal shaft;

inserting the first mandrel into the lumen of the inner shaft;

disposing the outer proximal shaft such that a distal side of the inner shaft is disposed in the lumen of the outer distal shaft and a proximal side of the inner shaft is disposed on an outer surface of the outer proximal shaft;

inserting the second mandrel into the lumen of the outer distal shaft and the lumen of the outer proximal shaft;

disposing a heat shrinkable tube to cover a proximal end of the outer distal shaft, a distal end of the outer proximal shaft, and the inner shaft;

positioning a proximal end of the heat shrinkable tube closer to a distal side than a proximal end of the inner shaft; and joining the outer distal shaft, the outer proximal shaft, and the inner shaft to each other in a state where the heat shrinkable tube is shrunk by applying heat to the heat shrinkable tube, and wherein the proximal end of the inner shaft is not joined by the heat shrinkable tube to the outer surface of the outer proximal shaft.

15. The method for manufacturing the medical elongated body according to claim 14, wherein after the outer distal shaft, the outer proximal shaft, and the inner shaft are joined together, the inner shaft has a first region in which the inner shaft is joined to the outer proximal shaft, and a second region which is disposed on a proximal side of the first region and in which the inner shaft is not joined to the outer proximal shaft, in a range from the proximal end of the outer distal shaft disposed in an outer surface of an outer shaft covering a part of the inner shaft to the proximal end of the inner shaft, the method further comprising:

obliquely cutting a proximal portion of the inner shaft across the first region and the second region to form an inclined portion inclined from the first region toward the second region.

16. The method for manufacturing the medical elongated body according to claim 15, further comprising:

pulling the first mandrel out from the lumen of the inner shaft before cutting the proximal portion of the inner shaft.

17. The method for manufacturing the medical elongated body according to claim 15, wherein when the inclined portion is formed, the method further comprising:

cutting the inner shaft such that in an axial cross-section of the inner shaft, an axial length of the second region of the inclined portion is shorter than an axial length of the first region of the inclined portion.

* * * * *